US008460674B2

(12) United States Patent
Koelle

(10) Patent No.: US 8,460,674 B2
(45) Date of Patent: Jun. 11, 2013

(54) HSV-1 EPITOPES AND METHODS FOR USING SAME

(75) Inventor: David M. Koelle, Seattle, WA (US)

(73) Assignee: University of Washington, Seattle, WA (US)

(*) Notice: Subject to any disclaimer, the term of this patent is extended or adjusted under 35 U.S.C. 154(b) by 396 days.

(21) Appl. No.: 12/702,218

(22) Filed: Feb. 8, 2010

(65) Prior Publication Data

US 2010/0203073 A1 Aug. 12, 2010

Related U.S. Application Data

(60) Provisional application No. 61/150,753, filed on Feb. 7, 2009.

(51) Int. Cl.
| A61K 39/245 | (2006.01) |
| A61K 39/295 | (2006.01) |
| C07K 14/035 | (2006.01) |
| C07K 7/00 | (2006.01) |

(52) U.S. Cl.
USPC ............... 424/186.1; 424/192.1; 424/231.1; 435/69.3

(58) Field of Classification Search
None
See application file for complete search history.

(56) References Cited

U.S. PATENT DOCUMENTS

| 4,859,587 A | 8/1989 | Roizman |
| 5,538,724 A | 7/1996 | Butcher |
| 5,632,992 A | 5/1997 | Nesburn et al. |
| 5,714,152 A * | 2/1998 | Burke et al. ............... 424/231.1 |
| 6,375,952 B1 | 4/2002 | Koelle |
| 6,413,518 B1 | 7/2002 | Koelle |
| 6,534,261 B1 * | 3/2003 | Cox et al. .................... 435/6.12 |
| 6,814,969 B2 | 11/2004 | Koelle |
| 6,821,519 B2 | 11/2004 | Day et al. |
| 6,855,317 B2 | 2/2005 | Koelle |
| 6,962,709 B2 | 11/2005 | Koelle |
| 7,037,509 B2 | 5/2006 | Koelle |
| 7,078,041 B2 | 7/2006 | Koelle |
| 7,153,685 B2 * | 12/2006 | Mao et al. .................... 435/325 |
| 7,431,934 B2 | 10/2008 | Koelle |
| 7,666,434 B2 | 2/2010 | Koelle |
| 2002/0090610 A1 | 7/2002 | Hosken et al. |

FOREIGN PATENT DOCUMENTS

| NZ | 509974 | 2/2004 |
| WO | WO 92/02251 | 2/1992 |
| WO | WO 95/06055 | 3/1995 |
| WO | WO 95/16779 A | 6/1995 |
| WO | WO 97/05265 | 2/1997 |
| WO | WO 98/20016 | 5/1998 |
| WO | WO 01/23414 | 4/2001 |

OTHER PUBLICATIONS

Himmelein et al (Herpesviridae 2:5, pp. 1-10, 2011).*
Spatz et al (Journal of Medical Virology 62:29-36, 2000).*
Bjornberg, et al., "dUTPase from Herpes Simplex Virus Type 1; Purification from Infected Green Monkey Kidney (Vero) Cells ... " Protein Expression and Purification, 1993, 4:149-159.
De Plaen, E., "Cloning of Genes Coding for Antigens Recognized by Cytolytic T Lymphocytes," Immunology Methods Manual, 1997, 692-718.
Dolan, A., The Genome Sequence of Herpes Simplex Virus Type 2, Journal of Virology, 1998, 72(3):2010-2021.
Fuhlbrigge, Robert C. et al., "Cutaneous lymphocyte antigen is a specialized form of PSGL-1 expressed on skin-homing T cells", Nature, Oct. 30, 1997, vol. 389, pp. 978-981.
Homey, B., "CCL27-CCRIO Interactions Regulate T Cell-mediated Skin Inflammation", Nature Medicine, Feb. 2002, 8(2), pp. 157-165.
Khan, Naeem et al., "Comparative Analysis of CD8+ T Cell Responses against Human Cytomegalovirus Proteins pp65 and Immediate Early 1 Shows Similarities in Precursor Frequency, Oligoclonality, and Phenotype", The Journal of Infectious Diseases, Mar. 2002, vol. 185, pp. 1025-1034.
Koelle, D.M., "CD8 CTL from Genital Herpes Simplex Lesions; Recognition of Viral Tegument and Immediate Early Proteins and Lysis of Infected Cutaneous Cells", Journal of Immunology, Mar. 2001, 166(6):4049-4058.
Koelle, D.M., "Expression of Cutaneous Lymphocyte-associated Antigen by CD8(+) T Cells Specific for a Skin-trophic Virus", The Journal of Clinical Investigation, Aug. 2002, 110(4):537-548.
Koelle, D.M., "Recognition of Herpes Simplex Virus Type 2 Tegument Proteins by CD4 T Cells ... " Jnl. of Virology, 1998, 72(9): 7476-7483.
Koelle, D.M., "The Roles of T Lymphocytes in Host Responses to Herpes Simplex Virus," Herpes, 1995, 2:83-88.
Koelle, D.M., "Clearance of HSV-2 from Recurrent Genital Lesions Correlates with Infiltration of HSV-Specific Cytotoxic T Lymphoctyes," The Journal of Clinical Investigation, 1998, 101(7):1500-1508.
Koelle, D.M., "Preferential Presentation of Herpes Simplex Virus T-Cell Antigen by HLA DQA1*0501/DQB1*0201 in Comparison to HLA DQA1*0201/DQB1*0201," Human Immunology, 1997, 53(2):195-205.
Koelle, D.M., "Direct Recovery of Herpes Simplex Virus (HSV)-Specific T Lymphocyte Clones from Recurrent Genital HSV-2 Lesions," The Journal of Infectious Diseases, 1994, 169:956-61.
Koelle, D.M.., "Antigenic Specificities of Human CD+T-Cell Clones Recovered from Recurrent Genital Herpes Simples Virus Type 2 Lesions," Journal of Virology, 1994, 68(5):2803-2810.
Kwok, W.W., "Peptide Binding Affinity and pH Variation Establish Functional Thresholds for Activation of HLA-DQ-Restricted T Cell Recognition," Human Immunology, 1999, 60(7):619-626.

(Continued)

*Primary Examiner* — Mary E Mosher
(74) *Attorney, Agent, or Firm* — Karen S. Canady; canady + lortz LLP

(57) ABSTRACT

The invention provides HSV antigens and epitopes that are useful for the prevention and treatment of HSV infection. T-cells having specificity for antigens of the invention have demonstrated cytotoxic activity against cells loaded with virally-encoded peptide epitopes, and in many cases, against cells infected with HSV. The identification of immunogenic antigens responsible for T-cell specificity provides improved anti-viral therapeutic and prophylactic strategies. Compositions containing antigens or polynucleotides encoding antigens of the invention provide effectively targeted vaccines for prevention and treatment of HSV infection.

16 Claims, 6 Drawing Sheets

OTHER PUBLICATIONS

Marshall, Natalie A., "Rapid reconstitution of Epstein-Barr virus-specific T lymphocytes following allogeneic stem cell transplantation", Immunology, Oct. 15, 2000, Blood, vol. 96, No. 8, pp. 2814-2821.

Nozawa, Naoki, "Identification and Characterization of the UL7 Gene Product of Herpes Simplex Virus Type 2", Virus Genes, Jun. 2002, 24(3):257-266.

Paoletti, "Applications of Pox Virus Vectors to Vaccination: An Update," Proceedings of the National Academy of Science USA, Oct. 1996, 93:11349-11353.

Pober, Jordan S. et al., "Human Endothelial Cell Presentation of Antigen and the Homing of Memory/Effector T Cells to Skin", Annals New York Academy of Sciences, 2001, vol. 941, pp. 12-25.

Posavad, C.M., "High Frequency of CD8+ Cytotoxic T-Lymphocyte Precursors Specific for Herpes Simplex Viruses in Persons with Genital Herpes," Journal of Virology, 1996, 70(11):8165-8168.

Reichstetter, S., "MCH-Peptide Ligand Interactions Establish a Functional Threshold for Antigen-Specific T Cell Recognition," Human Immunology, 1999, 60(7):608-618.

Roizman, B., "Herpes Simplex Viruses and Their Replication", Fundamental Virology, $2^{nd}$ Edition, ed. Fields et al, Raven Press, 1991, New York, pp. 849-895.

Stanberry, "Glycoprotein-D-Adjuvant Vaccine to Prevent Genital Herpes," N. Engl. J. Med., 2002, 347(21):1652-1661.

Stanberry, Lawrence R., "Prospects for Control of Herpes Simplex Virus Disease through Immunization", Clinical Infectious Diseases, Mar. 2000, vol. 30, pp. 549-566.

Tatman, J.D. et al., "Assembly of Herpes Simplex Virus Type 1 Using a Panel of Recombinant Baculoviruses", J. of General Virology, 1994, 75, pp. 1101-1113.

Tigges, M.A., "Human CD8+ Herpes Simplex Virus-Specific Cytotoxic T-Lymphocyte Clones Recognize Diverse Virion Protein Antigens," Journal of Virology, 1992, 66(3):1622-1634.

Williams, "Characterization of a Herpes Simplex Virus Type 2 Deoxyuridine . . . " Virology, 1987, 156:282-292.

Williams, "Deoxyuridine Triphosphate Nucleotidohydrolase Induced by Herpes Simplex Virus Type 1," Jnl. of Biological Chemistry, 1984, 259(16): 10080-10084.

* cited by examiner ical field of the invention

SEQUENCE LISTING

```
<160> NUMBER OF SEQ ID NOS: 13

<210> SEQ ID NO 1
<211> LENGTH: 490
<212> TYPE: PRT
<213> ORGANISM: HSV-1

<400> SEQUENCE: 1

Met Asp Leu Leu Val Asp Glu Leu Phe Ala Asp Met Asn Ala Asp Gly
1               5                   10                  15

Ala Ser Pro Pro Pro Arg Pro Ala Gly Gly Pro Lys Asn Thr Pro
            20                  25                  30

Ala Ala Pro Pro Leu Tyr Ala Thr Gly Arg Leu Ser Gln Ala Gln Leu
        35                  40                  45

Met Pro Ser Pro Pro Met Pro Val Pro Pro Ala Ala Leu Phe Asn Arg
    50                  55                  60

Leu Leu Asp Asp Leu Gly Phe Ser Ala Gly Pro Ala Leu Cys Thr Met
65                  70                  75                  80
```

```
Leu Asp Thr Trp Asn Glu Asp Leu Phe Ser Ala Leu Pro Thr Asn Ala
             85                  90                  95

Asp Leu Tyr Arg Glu Cys Lys Phe Leu Ser Thr Leu Pro Ser Asp Val
            100                 105                 110

Val Glu Trp Gly Asp Ala Tyr Val Pro Glu Arg Thr Gln Ile Asp Ile
            115                 120                 125

Arg Ala His Gly Asp Val Ala Phe Pro Thr Leu Pro Ala Thr Arg Asp
130                 135                 140

Gly Leu Gly Leu Tyr Tyr Glu Ala Leu Ser Arg Phe His Ala Glu
145                 150                 155                 160

Leu Arg Ala Arg Glu Glu Ser Tyr Arg Thr Val Leu Ala Asn Phe Cys
                165                 170                 175

Ser Ala Leu Tyr Arg Tyr Leu Arg Ala Ser Val Arg Gln Leu His Arg
            180                 185                 190

Gln Ala His Met Arg Gly Arg Asp Arg Asp Leu Gly Glu Met Leu Arg
            195                 200                 205

Ala Thr Ile Ala Asp Arg Tyr Tyr Arg Glu Thr Ala Arg Leu Ala Arg
210                 215                 220

Val Leu Phe Leu His Leu Tyr Leu Phe Leu Thr Arg Glu Ile Leu Trp
225                 230                 235                 240

Ala Ala Tyr Ala Glu Gln Met Met Arg Pro Asp Leu Phe Asp Cys Leu
                245                 250                 255

Cys Cys Asp Leu Glu Ser Trp Arg Gln Leu Ala Gly Leu Phe Gln Pro
            260                 265                 270

Phe Met Phe Val Asn Gly Ala Leu Thr Val Arg Gly Val Pro Ile Glu
            275                 280                 285

Ala Arg Arg Leu Arg Glu Leu Asn His Ile Arg Glu His Leu Asn Leu
290                 295                 300

Pro Leu Val Arg Ser Ala Ala Thr Glu Glu Pro Gly Ala Pro Leu Thr
305                 310                 315                 320

Thr Pro Pro Thr Leu His Gly Asn Gln Ala Arg Ala Ser Gly Tyr Phe
                325                 330                 335

Met Val Leu Ile Arg Ala Lys Leu Asp Ser Tyr Ser Ser Phe Thr Thr
            340                 345                 350

Ser Pro Ser Glu Ala Val Met Arg Glu His Ala Tyr Ser Arg Ala Arg
            355                 360                 365

Thr Lys Asn Asn Tyr Gly Ser Thr Ile Glu Gly Leu Leu Asp Leu Pro
370                 375                 380

Asp Asp Asp Ala Pro Glu Glu Ala Gly Leu Ala Ala Pro Arg Leu Ser
385                 390                 395                 400

Phe Leu Pro Ala Gly His Thr Arg Arg Leu Ser Thr Ala Pro Pro Thr
                405                 410                 415

Asp Val Ser Leu Gly Asp Glu Leu His Leu Asp Gly Glu Asp Val Ala
            420                 425                 430

Met Ala His Ala Asp Ala Leu Asp Asp Phe Asp Leu Asp Met Leu Gly
            435                 440                 445

Asp Gly Asp Ser Pro Gly Pro Gly Phe Thr Pro His Asp Ser Ala Pro
450                 455                 460

Tyr Gly Ala Leu Asp Met Ala Asp Phe Glu Phe Glu Gln Met Phe Thr
465                 470                 475                 480

Asp Ala Leu Gly Ile Asp Glu Tyr Gly Gly
                485                 490
```

```
<210> SEQ ID NO 2
<211> LENGTH: 224
<212> TYPE: PRT
<213> ORGANISM: HSV-1

<400> SEQUENCE: 2

Met Gly Ile Leu Gly Trp Val Gly Leu Ile Ala Val Gly Ile Leu Cys
1               5                   10                  15

Val Arg Gly Gly Leu Pro Ser Thr Glu Tyr Val Ile Arg Ser Arg Val
            20                  25                  30

Ala Arg Glu Val Gly Asp Ile Leu Lys Val Pro Cys Val Pro Leu Pro
        35                  40                  45

Ser Asp Asp Leu Asp Trp Arg Tyr Glu Thr Pro Ser Ala Ile Asn Tyr
    50                  55                  60

Ala Leu Ile Asp Gly Ile Phe Leu Arg Tyr His Cys Pro Gly Leu Asp
65                  70                  75                  80

Thr Val Leu Trp Asp Arg His Ala Gln Arg Ala Tyr Trp Val Asn Pro
                85                  90                  95

Phe Leu Phe Gly Ala Gly Phe Leu Glu Asp Leu Ser His Pro Ala Phe
            100                 105                 110

Pro Ala Asp Thr Gln Glu Thr Glu Thr Arg Leu Ala Leu Tyr Lys Glu
        115                 120                 125

Ile Arg Gln Ala Leu Asp Ser Arg Lys Gln Ala Ser His Thr Pro
    130                 135                 140

Val Lys Ala Gly Cys Val Asn Phe Asp Tyr Ser Arg Thr Arg Arg Cys
145                 150                 155                 160

Val Gly Arg Gln Asp Leu Gly Leu Thr Asn Arg Thr Ser Gly Arg Thr
                165                 170                 175

Pro Val Leu Pro Ser Asp Asp Glu Ala Gly Leu Gln Pro Lys Pro Leu
            180                 185                 190

Thr Thr Pro Ser Pro Ile Ile Ala Thr Ser Asp Pro Thr Pro Arg Arg
        195                 200                 205

Asp Ala Ala Thr Lys Ser Arg Arg Arg Pro His Phe Arg Gly Leu
    210                 215                 220

<210> SEQ ID NO 3
<211> LENGTH: 338
<212> TYPE: PRT
<213> ORGANISM: HSV-1

<400> SEQUENCE: 3

Met Leu Ala Val Arg Ser Leu Gln His Leu Ser Thr Val Val Leu Ile
1               5                   10                  15

Thr Ala Tyr Gly Leu Val Leu Val Trp Tyr Thr Val Phe Gly Ala Ser
            20                  25                  30

Pro Leu His Arg Cys Ile Tyr Val Val Arg Pro Thr Gly Thr Asn Asn
        35                  40                  45

Asp Thr Ala Leu Val Trp Met Lys Met Asn Gln Thr Leu Leu Phe Leu
    50                  55                  60

Gly Ala Pro Thr His Pro Pro Asn Gly Gly Trp Arg Asn His Ala His
65                  70                  75                  80

Ile Ser Tyr Ala Asn Leu Ile Ala Gly Arg Val Val Pro Phe Gln Val
                85                  90                  95

Pro Pro Asp Ala Met Asn Arg Arg Ile Met Asn Val His Glu Ala Val
            100                 105                 110

Asn Cys Leu Glu Thr Leu Trp Tyr Thr Arg Val Arg Leu Val Val Val
        115                 120                 125
```

-continued

```
Gly Trp Phe Leu Tyr Leu Ala Phe Val Ala Leu His Gln Arg Arg Cys
            130                 135                 140

Met Phe Gly Val Val Ser Pro Ala His Lys Met Val Ala Pro Ala Thr
145                 150                 155                 160

Tyr Leu Leu Asn Tyr Thr Gly Arg Ile Val Ser Ser Val Phe Leu Gln
                165                 170                 175

Tyr Pro Tyr Thr Lys Ile Thr Arg Leu Leu Cys Glu Leu Ser Val Gln
            180                 185                 190

Arg Gln Asn Leu Val Gln Leu Phe Glu Thr Asp Pro Val Thr Phe Leu
        195                 200                 205

Tyr His Arg Pro Ala Ile Gly Val Ile Val Gly Cys Glu Leu Ile Val
    210                 215                 220

Arg Phe Val Ala Val Gly Leu Ile Val Gly Thr Ala Phe Ile Ser Arg
225                 230                 235                 240

Gly Ala Cys Ala Ile Thr Tyr Pro Leu Phe Leu Thr Ile Thr Thr Trp
                245                 250                 255

Cys Phe Val Ser Thr Ile Gly Leu Thr Glu Leu Tyr Cys Ile Leu Arg
            260                 265                 270

Arg Gly Pro Ala Pro Lys Asn Ala Asp Lys Ala Ala Pro Gly Arg
        275                 280                 285

Ser Lys Gly Leu Ser Gly Val Cys Gly Arg Cys Cys Ser Ile Ile Leu
    290                 295                 300

Ser Gly Ile Ala Met Arg Leu Cys Tyr Ile Ala Val Val Ala Gly Val
305                 310                 315                 320

Val Leu Val Ala Leu His Tyr Glu Gln Glu Ile Gln Arg Arg Leu Phe
                325                 330                 335

Asp Val

<210> SEQ ID NO 4
<211> LENGTH: 10
<212> TYPE: PRT
<213> ORGANISM: HSV-1

<400> SEQUENCE: 4

Ser Ala Leu Pro Thr Asn Ala Asp Leu Tyr
1               5                   10

<210> SEQ ID NO 5
<211> LENGTH: 10
<212> TYPE: PRT
<213> ORGANISM: HSV-1

<400> SEQUENCE: 5

Phe Thr Asp Ala Leu Gly Ile Asp Glu Tyr
1               5                   10

<210> SEQ ID NO 6
<211> LENGTH: 9
<212> TYPE: PRT
<213> ORGANISM: HSV-1

<400> SEQUENCE: 6

Glu Thr Asp Pro Val Thr Phe Leu Tyr
1               5

<210> SEQ ID NO 7
<211> LENGTH: 9
<212> TYPE: PRT
<213> ORGANISM: HSV-1
```

```
<400> SEQUENCE: 7

Leu Ile Asp Gly Ile Phe Leu Arg Tyr
1               5

<210> SEQ ID NO 8
<211> LENGTH: 9
<212> TYPE: PRT
<213> ORGANISM: HSV-2

<400> SEQUENCE: 8

Glu Ala Asp Pro Val Thr Phe Leu Tyr
1               5

<210> SEQ ID NO 9
<211> LENGTH: 9
<212> TYPE: PRT
<213> ORGANISM: HSV-2

<400> SEQUENCE: 9

Arg Ile Asp Gly Ile Phe Leu Arg Tyr
1               5

<210> SEQ ID NO 10
<211> LENGTH: 13
<212> TYPE: PRT
<213> ORGANISM: HSV-1

<400> SEQUENCE: 10

Val Arg Gln Leu His Arg Gln Ala His Met Arg Gly Arg
1               5                   10

<210> SEQ ID NO 11
<211> LENGTH: 13
<212> TYPE: PRT
<213> ORGANISM: HSV-1

<400> SEQUENCE: 11

His Arg Gln Ala His Met Arg Gly Arg Asp Arg Asp Leu
1               5                   10

<210> SEQ ID NO 12
<211> LENGTH: 13
<212> TYPE: PRT
<213> ORGANISM: HSV-1

<400> SEQUENCE: 12

Tyr Tyr Arg Glu Thr Ala Arg Leu Ala Arg Val Leu Phe
1               5                   10

<210> SEQ ID NO 13
<211> LENGTH: 12
<212> TYPE: PRT
<213> ORGANISM: HSV-1

<400> SEQUENCE: 13

Thr Ala Arg Leu Ala Arg Val Leu Phe Leu His Leu
1               5                   10
```

HSV-1 EPITOPES AND METHODS FOR USING SAME

This application claims the benefit of U.S. provisional patent application No. 61/150,753, filed Feb. 7, 2009, the entire contents of which are incorporated herein by reference.

STATEMENT REGARDING FEDERALLY SPONSORED RESEARCH

This invention was made with government support under grant number AI50132 and 1 R21 081060 awarded by the National Institutes of Health. The government has certain rights in the invention.

TECHNICAL FIELD OF THE INVENTION

The invention relates to molecules, compositions and methods that can be used for the treatment and prevention of viral infection and other diseases. More particularly, the invention identifies epitopes of herpes simplex virus type 1 (HSV-1) proteins that can be used for methods involving molecules and compositions having the antigenic specificity of HSV-specific T cells. In addition, the invention relates to methods for detecting, treating and preventing HSV infection, as well as methods for inducing an immune response to HSV. The epitopes described herein are also useful in the development of diagnostic and therapeutic agents for detecting, preventing and treating viral infection and other diseases.

BACKGROUND OF THE INVENTION

Herpes simplex type 1 (HSV-1) infects about 60% of people in the United States. Most people have either no symptoms or bothersome recurrent sores on the lips or face. Medically serious consequences of HSV-1 include herpes simplex encephalitis (HSE). HSE is usually a recurrent of HSV-1, and occurs in otherwise healthy, immunocompetent people. HSE can be fatal, and typically results in long term brain damage. Herpes simplex keratitis (HSK) is another serious consequence. HSK is part of a spectrum of HSV eye diseases that consume considerable health care resources; HSK can lead to blindness and a need for corneal transplantation. These and other complications are rare on a per-patient basis, but given the high prevalence of HSV-1, overall have a significant health care impact.

There is no HSV-1 vaccine. Recently, mouse labs discovered that immune cells termed HSV-1-specific CD8 T-cells are located at the anatomic site within which HSV-1 resides in a latent, lifelong state. This location is the trigeminal ganglia (TG), which in humans is a kidney-bean sized bit of nerve tissue deep in the bones of the face (left and right side). In the TG, occasional reactivation events take place after which HSV-1 migrates down nerve cells to the skin of the face, the eyes (HSK), or sometimes the lining of the brain (HSE). Mouse studies have shown that an immunologic battle is taking place in the TG, in which highly specific T-cells that recognize discrete, 8-10 amino acid long bits of HSV-1 proteins (epitopes) physically surround HSV-1-infected neurons.

There are no data concerning which of the about 85 HSV-1 genes are actually expressed at the protein level in the TG. Dogma is that new viral particles are assembled somehow in permanently infected neurons in the TG, and then transport down axons to peripheral tissues (skin, eye) or to brain (HSE). It was not previously thought that enough HSV-1 protein was expressed in the right way such that the immune system could recognize this infection in the TG. Nervous system tissue in general is considered "immune silent" and behind a blood-brain barrier, with the body having strong reasons to limit inflammatory damage near irreplaceable neurons.

There remains a need, however, to identify epitopes that can be used for effective vaccines for treatment and/or prevention of HSV infection.

SUMMARY OF THE INVENTION

The invention provides HSV antigens, polypeptides comprising HSV antigens, polynucleotides encoding the polypeptides, vectors, and recombinant viruses containing the polynucleotides, antigen-presenting cells (APCs) presenting the polypeptides, immune cells directed against HSV, and pharmaceutical compositions. In particular, the invention provides HSV-1 antigens. In some embodiments, the antigens are specific to HSV-1 as compared to HSV-2. The pharmaceutical compositions can be used both prophylactically and therapeutically. The invention additionally provides methods, including methods for preventing and treating HSV infection, for killing HSV-infected cells, for inhibiting viral replication, for enhancing secretion of antiviral and/or immunomodulatory lymphokines, and for enhancing production of HSV-specific antibody. For preventing and treating HSV infection, for enhancing secretion of antiviral and/or immunomodulatory lymphokines, for enhancing production of HSV-specific antibody, and generally for stimulating and/or augmenting HSV-specific immunity, the method comprises administering to a subject a polypeptide, polynucleotide, recombinant virus, APC, immune cell or composition of the invention. The methods for killing HSV-infected cells and for inhibiting viral replication comprise contacting an HSV-infected cell with an immune cell of the invention. The immune cell of the invention is one that has been stimulated by an antigen of the invention or by an APC that presents an antigen of the invention. A method for producing such immune cells is also provided by the invention. The method comprises contacting an immune cell with an APC, preferably a dendritic cell, that has been modified to present an antigen of the invention. In a preferred embodiment, the immune cell is a T cell such as a CD4+ or CD8+ T cell.

Specific HSV antigens that have been identified by the method of the invention include VP16 (product of UL48), glycoprotein L (product of UL1) and glycoprotein K (product of UL53) of HSV-1. In addition, immunologically active fragments and epitopes within these HSV-1 proteins have been identified, namely, amino acids 64-160, 90-99, 91-99, 141-240, 187-199, 191-203, 215-227, 219-230, 381-490, 477-490, 479-488, 479-489, 479-488, 480-488 of VP16, amino acids 66-74 of glycoprotein L, and amino acids 201-209 of glycoprotein K. The four epitopes, UL1 66-74, UL53 201-209, and UL48 90-99 and 479-488, are all strongly recognized by subjects who are healthy and have both HSV-1 infection and the A*0101 variant of the human gene HLA-A.

The diseases to be prevented or treated using compositions and methods of the invention include diseases associated with herpes virus infection, particularly HSV-1 infection. HSV-1 infections have considerable medical impact. Highlights include neonatal HSV-1 encephalitis and visceral infection leading to death or brain damage, HSV-1 encephalitis in adults, and a wide spectrum of HSV eye infections including acute retinal necrosis (ARN) and herpetic stromal keratitis (HSK). Medical care for these ocular complications is unsatisfactory The invention additionally provides pharmaceutical compositions comprising the HSV antigens and epitopes identified herein. Also provided is an isolated polynucleotide that encodes a polypeptide of the invention, and a composition comprising the polynucleotide. The invention additionally provides a recombinant virus genetically modified to express a polynucleotide of the invention, and a composition comprising the recombinant virus. In one embodiment, the recombinant virus is vaccinia virus, canary pox virus, HSV, lentivirus, retrovirus or adenovirus. A composition of the invention can be a pharmaceutical composition. The composition can optionally comprise a pharmaceutically acceptable carrier and/or an adjuvant.

BRIEF DESCRIPTION OF THE FIGURES

FIGS. 1A-1D are photomicrographs of consecutive human TG slides hybridized with a HSV-1 LAT oligonucleotide (1A) or stained for CD3 (1B); some LAT+ neurons (arrows) are not encircled with T cells (1C-1D). FIGS. 1C-1D are consecutive slides stained for CD8 (1C) or TIA-1 (1D). Sections were developed with 5-bromo-4-chloro-3-indolyl-phosphate (1A), 3-amino-9-ethylcarbazole chromogen (1B), or diaminobenzidine (1C-1D) that resulted in a black, red or brown color, respectively.

DETAILED DESCRIPTION OF THE INVENTION

Figures 1A, 1B:
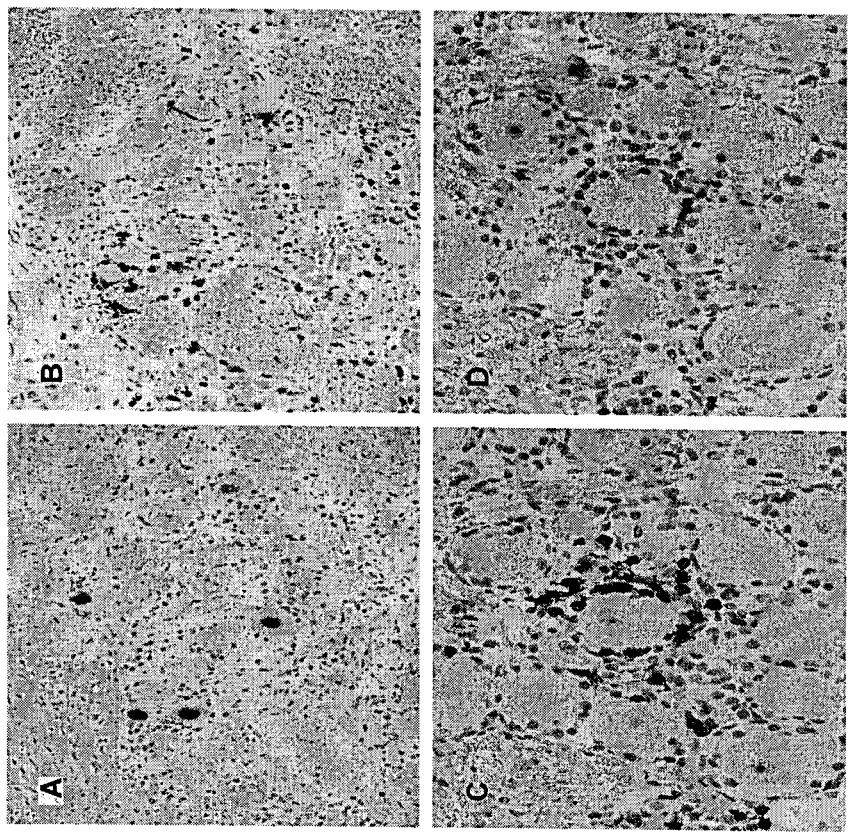

The invention described herein is based on the discovery of the HSV-1 open reading frames (antigens) and minimal units of recognition (epitopes) recognized by CD8 and CD4 T-cells in the TG of humans. An immortal cell line ("LCL") and T-cells from TG obtained from deceased individuals were used, in addition to a reagent set containing about 70% of the genes of HSV-1 individually cloned. This set was increased to 100% by cloning the rest of the HSV-1 genes. All the HSV-1 genes were transferred into a custom-made expression vector made from bits and pieces of two commercial vectors from Invitrogen, Inc. and one from Clontech, Inc. An established expression cloning technology (Koelle et al. J Immunol. 2001; Jing et al. J Immunol. 2005) was used to determine which HSV-1 open reading frames were recognized. We initially used "full length" HSV-1 genes, not fragments. Three initial "hits" were: Open reading frames UL1 (glycoprotein L), UL48 (VP16), and UL53 (glycoprotein K). We next determined the minimal fully active epitopes in these ORFs (usually 9 amino acids long): for glycoprotein L, amino acids 66-74, sequence LIDGIFLRY (SEQ ID NO: 6); for glycoprotein K, amino acids 201-209, sequence ETDPVTFLY (SEQ ID NO: 7); and for VP16, amino acids 90-99 and amino acids 479-488. These epitopes are recognized by CD8 T cells that were recovered from the human trigeminal ganglia (TG). Fragments of VP16 that are recognized by CD4 T cells were also identified: amino acids 141-240, 218-320, 187-199, 191-203, 215-227 and 219-230, suggesting that the epitopes are located at or near amino acids 191-199 and 219-227.

Immune system cells that can monitor, surveil and control HSV-1 reactivation at its site of origin, infected neurons in the TG, offer effective targets for vaccines. In a preventative mode, pre-equipping a patient with T-cells specific for those HSV-1 proteins that are expressed in TG could modify (reduce) initial and recurrent infection of TG neurons. In a therapeutic mode, a vaccine would boost levels of T-cells that are capable of sensing HSV-1 reactivation in TG neurons, and thereby down-regulate recurrent infection.

DEFINITIONS

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids, and can be at least about 15 amino acids. Typically, optimal immunological potency is obtained with lengths of 8-10 amino acids. Those skilled in the art also recognize that additional adjacent sequence from the original (native) protein can be included, and is often desired, in an immunologically effective polypeptide suitable for use as a vaccine. This adjacent sequence can be from 1, 2, 3, 4, 5, 6, 7, 8, 9 or 10 amino acids in length to as much as 15, 20, 25, 30, 35, 40, 45, 50, 75 or 100 amino acids in length or more. Adjacent native sequence may be included at one, both or neither end of the identified epitope for use in a vaccine composition.

As used herein, particularly in the context of polypeptides of the invention, "consisting essentially of" means the polypeptide consists of the recited amino acid sequence and, optionally, adjacent amino acid sequence, but less than the full-length protein from which the polypeptide is derived. The adjacent sequence typically consists of additional, adjacent amino acid sequence found in the full length antigen, but variations from the native antigen can be tolerated in this adjacent sequence while still providing an immunologically active polypeptide.

As used herein, "epitope" refers to a molecular region of an antigen capable of eliciting an immune response and of being specifically recognized by the specific immune T-cell produced by such a response. Another term for "epitope" is "determinant" or "antigenic determinant". Those skilled in the art often use the terms epitope and antigen interchangeably in the context of referring to the determinant against which an immune response is directed. A minimal epitope is the shortest antigenic region identified for a given antigenic polypeptide.

As used herein, "HSV polypeptide" includes HSV-1 and HSV-2, unless otherwise indicated. References to amino acids of HSV proteins or polypeptides are based on the genomic sequence information regarding HSV-1 (strain 17+) as described in McGeoch et al., 1988, J. Gen. Virol. 69:1531-1574.

As used herein, "substitutional variant" refers to a molecule having one or more amino acid substitutions or deletions in the indicated amino acid sequence, yet retaining the ability to be "immunologically active", or specifically recognized by an immune cell. The amino acid sequence of a substitutional variant is preferably at least 80% identical to the native amino acid sequence, or more preferably, at least 90% identical to the native amino acid sequence. Typically, the substitution is a conservative substitution.

One method for determining whether a molecule is "immunologically active", "immunologically effective", or can be specifically recognized by an immune cell, is the cytotoxicity assay described in D. M. Koelle et al., 1997, Human Immunol. 53:195-205. Other methods for determining whether a molecule can be specifically recognized by an immune cell are described in the examples provided hereinbelow, including the ability to stimulate secretion of interferon-gamma or the ability to lyse cells presenting the molecule. An immune cell will specifically recognize a molecule when, for example, stimulation with the molecule results in secretion of greater interferon-gamma than stimulation with control molecules. For example, the molecule may stimulate greater than 5 pg/ml, or preferably greater than 10 pg/ml, interferon-gamma secretion, whereas a control molecule will stimulate less than 5 pg/ml interferon-gamma.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "adjuvant" includes those adjuvants commonly used in the art to facilitate the stimulation of an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquilla); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

As used herein, to "prevent" or "protect against" a condition or disease means to hinder, reduce or delay the onset or progression of the condition or disease.

Overview

Herpes simplex virus type 1 (HSV-1) and HSV-2 are related alphaherpesviruses. Each has about 85 known ORFs. HSV-1/HSV-2 amino acid identity ranges from 20 to 90% depending on the ORF. Animal gene knockout and monoclonal antibody (mAb) blocking studies, and data from immune-suppressed humans, suggest vital roles for CD4 and CD8 T-cells in the control of primary and recurrent HSV. CD8 T-cells usually recognize unmodified 8-10 amino acid epitopes. T-cell clonotypes can be either type-common, recognizing HSV-1 and HSV-2, or type-specific. Most HSV-specific CD8 and CD4 T-cell epitopes to date have been type-specific. Human HSV T-cell research has concentrated on HSV-2. This invention concerns the less-studied human T-cell response to HSV-1.

(SEQ ID NO: 1), glycoprotein L (SEQ ID NO: 2), glycoprotein K (SEQ ID NO: 3), or a fragment or combination thereof. In some representative embodiments, the fragment comprises amino acids 64-160, 90-99 (SALPTNADLY; SEQ ID NO: 4), 91-99, 141-240, 187-199, 191-203, 218-320, 215-227, 219-230, 381-490, 477-490, 479-488, 479-489, 479-488 (FTDALGIDEY; SEQ ID NO: 5), 480-488 of VP16, amino acids 66-74 of glycoprotein L (ETDPVTFLY; SEQ ID NO: 6 or EADPVTFLY; SEQ ID NO: 8), or amino acids 201-209 of glycoprotein K (LIDGI FLRY; SEQ ID NO: 7 or RIDGIFLRY; SEQ ID NO: 9).

```
UL48/VP16
                                                                     (SEQ ID NO: 1)
  1 mdllvdelfa dmnadgaspp pprpaggpkn tpaapplyat grlsqaqlmp sppmpvppaa
 61 lfnrllddlg fsagpalctm ldtwnedlfs alptnadlyr eckflstlps dvvewgdayv
121 pertqidira hgdvafptlp atrdglglyy ealsrffhae lrareesyrt vlanfcsaly
181 rylrasvrql hrqahmrgrd rdlgemlrat iadryyreta rlarvlflhl ylfltreilw
241 aayaeqmmrp dlfdclccdl eswrqlaglf qpfmfvngal tvrgvpiear rlrelnhire
301 hlnlplvrsa ateepgaplt tpptlhgnqa rasgyfmvli rakldsyssf ttspseavmr
361 ehaysrartk nnygstiegl ldlpdddape eaglaaprls flpaghtrrl stapptdvsl
421 gdelhldged vamahadald dfdldmlgdg dspgpgftph dsapygaldm adfefeqmft
481 dalgideygg UL1/Glycoprotein L
                                                                     (SEQ ID NO: 2)
  1 mgilgwvgli avgilcvrgg lpsteyvirs rvarevgdil kvpcvplpsd dldwryetps
 61 ainyalidgi flryhcpgld tvlwdrhaqr aywvnpflfg agfledlshp afpadtqete
121 trlalykeir qaldsrkqaa shtpvkagcv nfdysrtrrc vgrqdlgltn rtsgrtpvlp
181 sddeaglqpk plttpspiia tsdptprrda atksrrrrph frgl UL53/Glycoprotein K
                                                                     (SEQ ID NO: 3)
  1 mlavrslqhl stvvlitayg lvlvwytvfg asplhrciyv vrptgtnndt alvwmkmnqt
 61 llflgapthp pnggwrnhah isyanliagr vvpfqvppda mnrrimnvhe avncletlwy
121 trvrlvvvgw flylafvalh qrrcmfgvvs pahkmvapat yllnytgriv ssvflqypyt
181 kitrllcels vqrqnlvqlf etdpvtflyh rpaigvivgc elivrfvavg livgtafisr
241 gacaityplf ltittwcfvs tigltelyci lrrgpapkna dkaaapgrsk glsgvcgrcc
301 siilsgiamr lcyiavvagv vlvalhyeqe iqrrlfdv
```

HSV infections are thought to be permanent, due to infection of sensory ganglion neurons. Infection is most accurately diagnosed by IgG serology: patients remain seropositive for life. The prevalence of HSV-1 infection is about 70% in diverse human populations. There is a great spectrum in the severity of HSV infections. Only a minority of persons with HSV corneal infection progress to blinding HSK. This is likely attributable at least in part to bona fide biological variation. Inoculum size is important in some HSV animal models. Inter-strain sequence divergence is of uncertain clinical significance. Divergent clinical severities in persons proven to have the same HSV strain argues a dominant effect. The invention addresses a need for treatment and prevention of HSV-1 infection.

HSV Polypeptides

In one embodiment, the invention provides an isolated HSV polypeptide. The polypeptide comprises a VP16 protein A fragment of the invention consists of less than the complete amino acid sequence of the corresponding protein, but includes the recited epitope or antigenic region. As is understood in the art and confirmed by assays conducted using fragments of widely varying lengths, additional sequence beyond the recited epitope can be included without hindering the immunological response. A fragment of the invention can be as few as 8 amino acids in length, or can encompass 10%, 20%, 30%, 40%, 50%, 60%, 70%, 80%, 90% or 95% of the full length of the protein.

The optimal length for the polypeptide of the invention will vary with the context and objective of the particular use, as is understood by those in the art. In some vaccine contexts, a full-length protein or large portion of the protein (e.g., up to 100 amino acids, 150 amino acids, 200 amino acids, 250 amino acids or more) provides optimal immunological stimulation, while in others, a short polypeptide (e.g., less than 50 amino acids, 40 amino acids, 30 amino acids, 20 amino acids, 15 amino acids or fewer) comprising the minimal epitope and/or a small region of adjacent sequence facilitates delivery and/or eases formation of a fusion protein or other means of combining the polypeptide with another molecule or adjuvant.

A polypeptide for use in a composition of the invention comprises a HSV polypeptide that contains an epitope or minimal stretch of amino acids sufficient to elicit an immune response. These polypeptides typically consist of such an epitope and, optionally, adjacent sequence. Those skilled in the art are aware that the HSV epitope can still be immunologically effective with a small portion of adjacent HSV or other amino acid sequence present. Accordingly, a typical polypeptide of the invention will consist essentially of the recited HSV epitope and have a total length of up to 15, 20, 25 or 30 amino acids.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. An isolated HSV polypeptide of the invention is one that has been isolated, produced or synthesized such that it is separate from a complete, native HSV virus, although the isolated polypeptide may subsequently be introduced into a recombinant HSV or other virus. A recombinant virus that comprises an isolated polypeptide or polynucleotide of the invention is an example of subject matter provided by the invention. Preferably, such isolated polypeptides are at least about 90% pure, more preferably at least about 95% pure and most preferably at least about 99% pure. A polynucleotide is considered to be isolated if, for example, it is cloned into a vector that is not part of the natural environment.

The polypeptide can be isolated from its naturally occurring form, produced by recombinant means or synthesized chemically. Recombinant polypeptides encoded by DNA sequences described herein can be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably the host cells employed are E. coli, yeast or a mammalian cell line such as Cos or CHO. Supernatants from the soluble host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Fragments and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain (Merrifield, 1963, J. Am. Chem. Soc. 85:2146-2149). Equipment for automated synthesis of polypeptides is commercially available from suppliers such as Perkin Elmer/Applied BioSystems Division (Foster City, Calif.), and may be operated according to the manufacturer's instructions.

Variants of the polypeptide for use in accordance with the invention can have one or more amino acid substitutions, deletions, additions and/or insertions in the amino acid sequence indicated that result in a polypeptide that retains the ability to elicit an immune response to HSV or HSV-infected cells. Such variants may generally be identified by modifying one of the polypeptide sequences described herein and evaluating the reactivity of the modified polypeptide using a known assay such as a T cell assay described herein. Polypeptide variants preferably exhibit at least about 70%, more preferably at least about 90%, and most preferably at least about 95% identity to the identified polypeptides. These amino acid substitutions include, but are not necessarily limited to, amino acid substitutions known in the art as "conservative".

A "conservative" substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

One can readily confirm the suitability of a particular variant by assaying the ability of the variant polypeptide to elicit an immune response. The ability of the variant to elicit an immune response can be compared to the response elicited by the parent polypeptide assayed under identical circumstances. One example of an immune response is a cellular immune response. The assaying can comprise performing an assay that measures T cell stimulation or activation. Examples of T cells include CD4 and CD8 T cells.

One example of a T cell stimulation assay is a cytotoxicity assay, such as that described in Koelle, D M et al., Human Immunol. 1997, 53; 195-205. In one example, the cytotoxicity assay comprises contacting a cell that presents the antigenic viral peptide in the context of the appropriate HLA molecule with a T cell, and detecting the ability of the T cell to kill the antigen presenting cell. Cell killing can be detected by measuring the release of radioactive $^{51}$Cr from the antigen presenting cell. Release of $^{51}$Cr into the medium from the antigen presenting cell is indicative of cell killing. An exemplary criterion for increased killing is a statistically significant increase in counts per minute (cpm) based on counting of $^{51}$Cr radiation in media collected from antigen presenting cells admixed with T cells as compared to control media collected from antigen presenting cells admixed with media.

Fusion Proteins

The polypeptide can be a fusion protein. In one embodiment, the fusion protein is soluble. A soluble fusion protein of the invention can be suitable for injection into a subject and for eliciting an immune response. Within certain embodiments, a polypeptide can be a fusion protein that comprises multiple polypeptides as described herein, or that comprises at least one polypeptide as described herein and an unrelated sequence. In one example, the fusion protein comprises a HSV epitope described herein (with or without flanking adjacent native sequence) fused with non-native sequence. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., 1985, Gene 40:39-46; Murphy et al., 1986, Proc. Natl. Acad. Sci. USA 83:8258-8262; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al., 1997, New Engl. J. Med., 336:86-9).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenza virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In some embodiments, it may be desirable to couple a therapeutic agent and a polypeptide of the invention, or to couple more than one polypeptide of the invention. For example, more than one agent or polypeptide may be coupled directly to a first polypeptide of the invention, or linkers that provide multiple sites for attachment can be used. Alternatively, a carrier can be used. Some molecules are particularly suitable for intercellular trafficking and protein delivery, including, but not limited to, VP22 (Elliott and O'Hare, 1997, Cell 88:223-233; see also Kim et al., 1997, J. Immunol. 159:1666-1668; Rojas et al., 1998, Nature Biotechnology 16:370; Kato et al., 1998, FEBS Lett. 427(2):203-208; Vives et al., 1997, J. Biol. Chem. 272(25):16010-7; Nagahara et al., 1998, Nature Med. 4(12):1449-1452).

A carrier may bear the agents or polypeptides in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088).

Polynucleotides, Vectors, Host Cells and Recombinant Viruses

The invention provides polynucleotides that encode one or more polypeptides of the invention. The polynucleotide can be included in a vector. The vector can further comprise an expression control sequence operably linked to the polynucleotide of the invention. In some embodiments, the vector includes one or more polynucleotides encoding other molecules of interest. In one embodiment, the polynucleotide of the invention and an additional polynucleotide can be linked so as to encode a fusion protein.

Within certain embodiments, polynucleotides may be formulated so to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, vaccinia or a pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

The invention also provides a host cell transformed with a vector of the invention. The transformed host cell can be used in a method of producing a polypeptide of the invention. The method comprises culturing the host cell and recovering the polypeptide so produced. The recovered polypeptide can be purified from culture supernatant.

Vectors of the invention can be used to genetically modify a cell, either in vivo, ex vivo or in vitro. Several ways of genetically modifying cells are known, including transduction or infection with a viral vector either directly or via a retroviral producer cell, calcium phosphate precipitation, fusion of the recipient cells with bacterial protoplasts containing the DNA, treatment of the recipient cells with liposomes or microspheres containing the DNA, DEAE dextran, receptor-mediated endocytosis, electroporation, micro-injection, and many other techniques known to those of skill. See, e.g., Sambrook et al. Molecular Cloning—A Laboratory Manual (2nd ed.) 1-3, 1989; and Current Protocols in Molecular Biology, F. M. Ausubel et al., eds., Greene Publishing Associates, Inc. and John Wiley & Sons, Inc., (1994 Supplement).

Examples of viral vectors include, but are not limited to retroviral vectors based on, e.g., HIV, SIV, and murine retroviruses, gibbon ape leukemia virus and other viruses such as adeno-associated viruses (AAVs) and adenoviruses. (Miller et al. 1990, Mol. Cell Biol. 10:4239; J. Kolberg 1992, NIH Res. 4:43, and Cornetta et al. 1991, Hum. Gene Ther. 2:215). Widely used retroviral vectors include those based upon murine leukemia virus (MuLV), gibbon ape leukemia virus (GaLV), ecotropic retroviruses, simian immunodeficiency virus (SIV), human immunodeficiency virus (HIV), and combinations. See, e.g. Buchscher et al. 1992, J. Virol. 66(5): 2731-2739; Johann et al. 1992, J. Virol. 66(5):1635-1640; Sommerfelt et al. 1990, Virol. 176:58-59; Wilson et al. 1989, J. Virol. 63:2374-2378; Miller et al. 1991, J. Virol. 65:2220-2224, and Rosenberg and Fauci 1993 in Fundamental Immunology, Third Edition, W. E. Paul (ed.) Raven Press, Ltd., New York and the references therein; Miller et al. 1990, Mol. Cell. Biol. 10:4239; R. Kolberg 1992, J. NIH Res. 4:43; and Cornetta et al. 1991, Hum. Gene Ther. 2:215.

In vitro amplification techniques suitable for amplifying sequences to be subcloned into an expression vector are known. Examples of such in vitro amplification methods, including the polymerase chain reaction (PCR), ligase chain reaction (LCR), Q13-replicase amplification and other RNA polymerase mediated techniques (e.g., NASBA), are found in Sambrook et al. 1989, Molecular Cloning—A Laboratory Manual (2nd Ed) 1-3; and U.S. Pat. No. 4,683,202; PCR Protocols A Guide to Methods and Applications (Innis et al. eds.) Academic Press Inc. San Diego, Calif. 1990. Improved methods of cloning in vitro amplified nucleic acids are described in U.S. Pat. No. 5,426,039.

The invention additionally provides a recombinant microorganism genetically modified to express a polynucleotide of the invention. The recombinant microorganism can be useful as a vaccine, and can be prepared using techniques known in the art for the preparation of live attenuated vaccines. Examples of microorganisms for use as live vaccines include, but are not limited to, viruses and bacteria. In a preferred embodiment, the recombinant microorganism is a virus. Examples of suitable viruses include, but are not limited to, vaccinia virus and other poxviruses.

Compositions

The invention provides compositions that are useful for treating and preventing HSV infection. The compositions can be used to inhibit viral replication and to kill virally-infected cells. In one embodiment, the composition is a pharmaceutical composition. The composition can comprise a therapeutically or prophylactically effective amount of a polypeptide, polynucleotide, recombinant virus, APC or immune cell of the invention. An effective amount is an amount sufficient to elicit or augment an immune response, e.g., by activating T cells. One measure of the activation of T cells is a cytotoxicity assay, as described in D. M. Koelle et al., 1997, Human Immunol. 53:195-205. In some embodiments, the composition is a vaccine.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

The composition of the invention can further comprise one or more adjuvants. Examples of adjuvants include, but are not limited to, helper peptide, alum, Freund's, muramyl tripeptide phosphatidyl ethanolamine or an immunostimulating complex, including cytokines. In some embodiments, such as with the use of a polynucleotide vaccine, an adjuvant such as a helper peptide or cytokine can be provided via a polynucleotide encoding the adjuvant. Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other viral antigens may be present, either incorporated into a fusion polypeptide or as a separate compound, within the composition or vaccine.

A pharmaceutical composition or vaccine may contain DNA encoding one or more of the polypeptides of the invention, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, 1998, Crit. Rev. Therap. Drug Carrier Systems 15:143-198, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317-321; Flexner et al., 1989, Ann. My Acad. Sci. 569:86-103; Flexner et al., 1990, Vaccine 8:17-21; U.S. Pat. Nos. 4,603,112, 4,769,330, and 5,017,487; WO 89/01973; U.S. Pat. No. 4,777,127; GB 2,200,651; EP 0,345,242: WO 91102805; Berkner, 1988, Biotechniques 6:616-627; Rosenfeld et al., 1991, Science 252:431-434; Kolls et al., 1994, Proc. Natl. Acad. Sci. USA 91:215-219; Kass-Eisler et al., 1993, Proc. Natl. Acad. Sci. USA 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA may also be "naked," as described, for example, in Ulmer et al., 1993, Science 259:1745-1749 and reviewed by Cohen, 1993, Science 259:1691-1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-13) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, 1989, Ann. Rev. Immunol. 7:145-173.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL™ adjuvants are available from Corixa Corporation (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets HSV-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have antiviral effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (Zitvogel et al., 1998, Nature Med. 4:594-600).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well-characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a polypeptide (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., 1997, Immunology and Cell Biology 75:456-460. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Administration of the Compositions

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals as well as other veterinary subjects. Preferably, the patients or subjects are human.

Compositions are typically administered in vivo via parenteral (e.g. intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue.

The compositions are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

The dose administered to a patient, in the context of the present invention should be sufficient to effect a beneficial therapeutic response in the patient over time, or to inhibit infection or disease due to infection. Thus, the composition is administered to a patient in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

The dose will be determined by the activity of the composition produced and the condition of the patient, as well as the body weight or surface areas of the patient to be treated. The size of the dose also will be determined by the existence, nature, and extent of any adverse side effects that accompany the administration of a particular composition in a particular patient. In determining the effective amount of the composition to be administered in the treatment or prophylaxis of diseases such as HSV infection, the physician needs to evaluate the production of an immune response against the virus, progression of the disease, and any treatment-related toxicity.

For example, a vaccine or other composition containing a subunit HSV protein can include 1-10,000 micrograms of HSV protein per dose. In a preferred embodiment, 10-1000 micrograms of HSV protein is included in each dose in a more preferred embodiment 10-100 micrograms of HSV protein dose. Preferably, a dosage is selected such that a single dose will suffice or, alternatively, several doses are administered over the course of several months. For compositions containing HSV polynucleotides or peptides, similar quantities are administered per dose.

In one embodiment, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an antiviral immune response, and is at least 10-50% above the basal (i.e., untreated) level. Such vaccines should also be capable of causing an immune response that leads to an improved clinical outcome in vaccinated patients as compared to non-vaccinated patients. In general, for pharmaceutical compositions and vaccines comprising one or more polypeptides, the amount of each polypeptide present in a dose ranges from about 0.1 µg to about 5 mg per kg of host. Preferably, the amount ranges from about 10 to about 1000 µg per dose. Suitable volumes for administration will vary with the size, age and immune status of the patient, but will typically range from about 0.1 mL to about 5 mL, with volumes less than about 1 mL being most common.

Compositions comprising immune cells are preferably prepared from immune cells obtained from the subject to whom the composition will be administered. Alternatively, the immune cells can be prepared from an HLA-compatible donor. The immune cells are obtained from the subject or donor using conventional techniques known in the art, exposed to APCs modified to present an epitope of the invention, expanded ex vivo, and administered to the subject. Protocols for ex vivo therapy are described in Rosenberg et al., 1990, New England J. Med. 9:570-578. In addition, compositions can comprise APCs modified to present an epitope of the invention.

Immune cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to enrich and rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., 1997, Immunological Reviews 157:177).

Administration by many of the routes of administration described herein or otherwise known in the art may be accomplished simply by direct administration using a needle, catheter or related device, at a single time point or at multiple time points.

Methods of Treatment and Prevention

The invention provides a method for treatment and/or prevention of HSV infection in a subject. The method comprises administering to the subject a composition of the invention. The composition can be used as a therapeutic or prophylactic vaccine. In one embodiment, the HSV is HSV-1. Alternatively, the HSV is HSV-2. The invention additionally provides a method for inhibiting viral replication, for killing virally-infected cells, for increasing secretion of lymphokines having antiviral and/or immunomodulatory activity, and for enhancing production of virus-specific antibodies. The method comprises contacting an infected cell with an immune cell directed against an antigen of the invention, for example, as described in the Examples presented herein. The contacting can be performed in vitro or in vivo. In a preferred embodiment, the immune cell is a T cell. T cells include CD4 and CD8 T cells. Compositions of the invention can also be used as a tolerizing agent against immunopathologic disease.

In addition, the invention provides a method of producing immune cells directed against HSV. The method comprises contacting an immune cell with a polypeptide of the invention. The immune cell can be contacted with the polypeptide via an antigen-presenting cell, wherein the antigen-presenting cell is modified to present an antigen included in a polypeptide of the invention. Preferably, the antigen-presenting cell is a dendritic cell. The cell can be modified by, for example, peptide loading or genetic modification with a nucleic acid sequence encoding the polypeptide. In one embodiment, the immune cell is a T cell. T cells include CD4 and CD8 T cells. Also provided are immune cells produced by the method. The immune cells can be used to inhibit viral replication, to kill virally-infected cells, in vitro or in vivo, to increase secretion of lymphokines having antiviral and/or immunomodulatory activity, to enhance production of virus-specific antibodies, or in the treatment or prevention of viral infection in a subject.

EXAMPLES

The following examples are presented to illustrate the present invention and to assist one of ordinary skill in making and using the same. The examples are not intended in any way to otherwise limit the scope of the invention.

Example 1

Discovery of HSV-1 T-Cell Antigens and Epitopes Recognized by Human TG-Infiltrating CD8 T-Cells Selective retention of HSV-1-specific T-cells in human TG. TG and blood were harvested a median of 5.5 hours postmortem (range, 4-10 hours). Serology was done to diagnose HSV-1 infection. A portion of each TG was used for DNA and RNA isolation. Most specimens from HSV-1-infected persons had HSV-1 DNA (median 3,321±879 copies/$10^5$ TG cells by PCR). TG of HSV-1-seronegative donors were PCR-negative for HSV-1. Within HSV-1 DNA (+) specimens, we detected LAT by RT-PCR (1). Immunohistology showed that HSV-1 seropositive donors had 2.1±0.4 CD3+ T-cells per neuron compared to 0.3±0.1 for HSV-1 uninfected donors (58). T-cell clusters were juxtaposed to HSV-1 LAT+ neurons (FIG. 1A-B). These clusters contained mainly CD8 T-cells expressing CD69, granzyme B and TIA-1 (119), consistent with activated cytotoxic T-cells (FIG. 1C-D) (2).

Cell suspensions were made from portions of TG using Liberase™ (Roche) and mesh filters. The TG CD8 T-cells expressed higher CD69 and lower CD45RA, CD28, CD27, CD62L, and CCR7 compared to paired PBMC-derived CD8 T-cells, consistent with activated, effector-memory T-cells (1). Direct ex vivo TCR spectratyping showed that TG-infiltrating T-cells were oligoclonal (1). The TG-derived T-cells were expanded polyclonally with the T-cell mitogen PHA. Importantly, TCRγ locus spectratyping results, using a published protocol (120), are consistent with the dominant T-cell populations in fresh TG tissue and expanded TG T-cell cultures being similar, as well as left-right similarity. This confirms that T-cell epitopes detected using expanded cell lines are relevant to the in vivo situation, and supports use of TCR Vβ gene family-specific mAb or riboprobes as back-up methods for staining HSV-1-specific CD8 T-cells in TG in situ.

Figure 2:
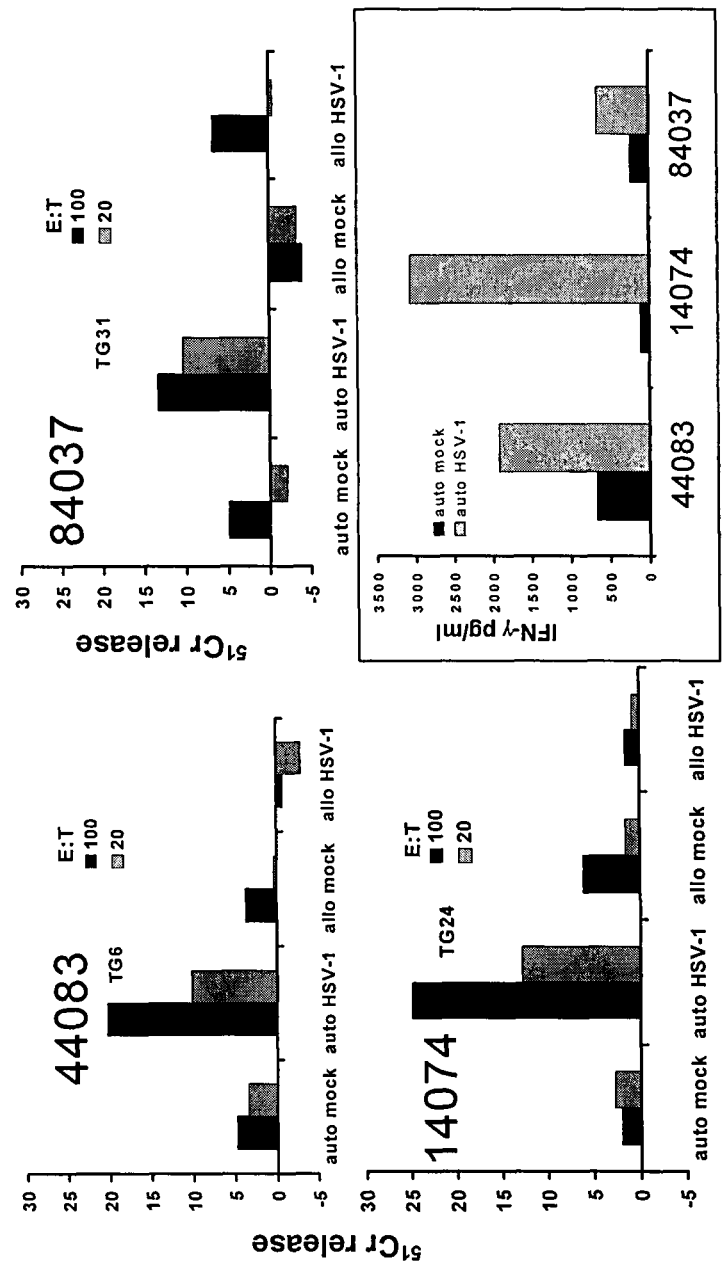
FIG. 2 is a set of bar graphs depicting results of using TG T-cell lines from 3 donors (44083, 14074, 84037) as effectors in $^{51}$Cr CTL assays using autologous (auto) or HLA-mismatched allogeneic (allo) LCL as targets. The box at the lower right shows that TG T-cells co-incubated with infected autologous LCL secrete IFN-γ.
Figure 3:
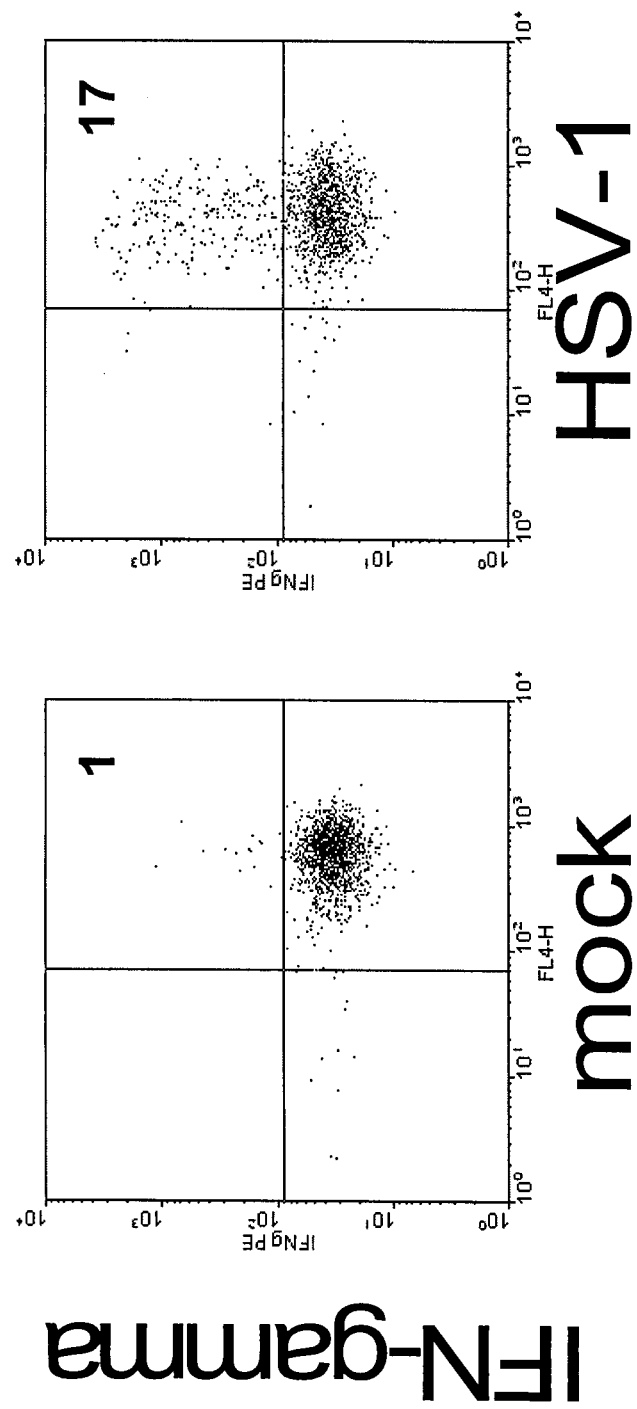
FIG. 3 plots the results of using TG-TCL of donor 14074 as responders in an intracellular IFN-γ assay with autologous mock- or HSV-1 infected LCL as APC. IFNγ is on the y-axis. Cells were gated on CD8(+) and CD3 is on the X-axis.

As published (1), the TG-TCL from HSV-1 DNA (+) specimens contained HSV-1-specific CD8 T-cells. Responses were confirmed by IFN-γ ELISPOT (1). TG-TCL were polyclonally expanded once with anti-CD3 (121). This mitogen (20) would not be expected to expand CD3-negative cells (e.g. natural killer cells: NK cells). We achieved ~1000-fold expansion of the TG T-cells, and cryopreserved ~40 aliquots. Autologous EBV-transformed B-cells (LCL) were HLA-typed. TG-TCL had specific CTL activity (FIG. 2) in [$^{51}$Cr]-cytotoxicity assays with autologous or HLA-mismatched LCL. As an added readout, 5×$10^5$ each TG-TCL and LCL were co-cultured for 24 hours. TG-TCL showed HSV-1-specific IFN-γ synthesis (FIG. 2). Negative control (no APC) and positive control (PMA/ionomycin) values were <20 and >4000 pg/ml. Intracellular cytokine cytometry (ICC) (101, 114, 115, 122), also showed strong CD8 T-cell recognition of HSV-1 (FIG. 3) (1). Overall, HSV-1-reactive CD8 T-cells are present in human TG at high enough levels for direct study without having to enrich them with the use of HSV-1 antigen.

CD8 T-cell antigen/epitope discovery methods. We have three recent process improvements to speed up viral T-cell antigen discovery: 1) use of polyclonal T-cell lines (TCL) rather than T-cell clones (TCC), 2) improved molecular libraries, and 3) use of a virtual ORFeome library. Our "Methods" paper reviews our process (121). The HSV genome (~152,000 base pairs, ~85 ORFs) is too large for cost-effective synthesis of every predicted peptide.

Our first process improvement is to use TCLs. For VV, we used TCLs amongst which >5% of CD8 T-cells are VV-specific. This level of enrichment produces an adequate signal/noise ratio, even when the TCLs are very poly-specific. We detected reactivity to 18 distinct CD8 T-cell epitopes within a single TCL (114, 123).

Our second improvement relates to viral DNA libraries (114, 115). Original methods used three libraries, offset by a single base pair to capture each ORF (20-22). New libraries are a single set of viral genomic DNA fragments expressed as eGFP fusions. In 96-well plates, we use "synthetic APC". Cos-7 cells receive HLA cDNA and pools of ~30 viral DNA fragments to generate cell surface HLA-peptide complexes. eGFP allows microscopic check of transfection efficiency. T-cells are added, and, if activated by cognate peptide/HLA complexes, release IFN-γ that is detected by ELISA. Positive pools are decoded to active single plasmids, which are sequenced to identify antigens as published (114, 121). Because these genomic libraries allow us to express (as fragments) unexpected ORFs, such as those that might occur within LAT or those that might be in alternate reading frames, we plan to probe TG-TCLs with both our virtual ORFeome (below) and a random HSV-1 genomic expression library.

Our third new method, a "virtual ORFeome" approach, was published for VV CD4 T-cell research (122) and is working in the HSV-1 CD8 T-cell system. It works in mice for CD8 T-cells (124-126). We PCR-cloned every VV ORF (n=180) and verified protein expression. Using responder cells and APC from vaccinees, we screened for reactivity with each VV ORF via [$^3$H]-thymidine incorporation. We found a clear discrimination between (+) and (−) responses (122). For HSV-1, 83 ORFs have already been cloned into a suitable expression vector.

To obtain T-cell activation, we require APC. We obtained ~10 ml blood at autopsy and reliably ($^{12}/_{12}$; 100%) generated LCL. LCL can be productively infected by HSV-1 and present endogenously synthesized HSV proteins efficiently to CD8 T-cells (30, 31, 110, 127, 128). We use LCL as "screening APC". If we observe specific CTL and IFN-γ signals (Table 1, FIG. 2, 3), we proceed to further workup. Synthetic APC are then used to screen viral proteomes. To make synthetic APC, we transfect Cos-7 cells with HLA class I heavy chain cDNA. Simian β2M/human HLA class I heterodimers reach the cell surface (loaded with peptides). We have cloned and validated cDNAs for >15 HLA A/B alleles (20, 22, 114) as reviewed (121).

TABLE 1

Human trigeminal ganglion-derived T cells recognize HSV-1.

| Donor no. | Virus in TG | Location | % IFN-γ+ T cells upon stimulation with HSV serotype-infected APC | | | |
|---|---|---|---|---|---|---|
| | | | HSV-1 | | HSV-2 | |
| | | | CD4+ | CD8+ | CD4+ | CD8+ |
| 14028 | HSV-1; | Left | 0 | 1.6 ± 0.1 | 0 | 0 |
| | VZV | Right | 0.2 ± 0.3 | 3.3 ± 0.4 | 0.4 ± 0.6 | 0 |
| 74083 | HSV-1 | Left | 0 | 9.9 ± 0.3 | 0 | 0 |
| | | Right | 0 | 6.3 ± 2.7 | 0.2 ± 0.1 | 0.3 ± 0.4 |
| 34045 | HSV-1; | Left | 1.9 ± 0.4 | 2.6 ± 0.7 | 0 | 0 |
| | VZV | Right | 3.7 ± 0.6 | 3.9 ± 1.2 | 0.3 ± 0.1 | 0 |
| 54047 | HSV-1; | Left | 0 | 0 | 0 | 0 |
| | VZV | Right | 0 | 0 | 0 | 0 |
| 84037 | HSV-1; | Left | 0 | 7.8 ± 1.6 | 0 | 0 |
| | VZV | Right | 0.3 ± 0.3 | 3.3 ± 0.3 | 0 | 0 |
| 44083 | HSV-1; | Left | 1.0 ± 0.6 | 4.7 ± 0.5 | 0.6 ± 0.5 | 0.5 ± 1.0 |
| | VZV | Right | 0.6 ± 0.5 | 5.4 ± 0 | 0.3 ± 0.5 | 0.2 ± 0.2 |
| 14074 | HSV-1; | Left | 0.4 ± 0.2 | 20.2 ± 5.5 | 0 | 1.2 ± 0.9 |
| | VZV | Right | NA | NA | NA | NA |
| 14046 | HSV-1; | Left | 1.4 ± 0.8 | 8.8 ± 1.9 | 0 | 1.1 ± 0.2 |
| | VZV | Right | NA | NA | NA | NA |
| 54004 | None | Left | 0.2 ± 0.4 | 0 | 0.4 ± 0.3 | 0 |
| | | Right | 0 | 0.2 ± 0.1 | 0 | 0 |
| 34034 | VZV | Left | 0.3 ± 0.2 | 0 | 0 | 0.4 ± 0.7 |
| | | Right | 0 | 0 | 0 | 0 |

"Virus in TG" indicates the virus-specific DNA detected in the TG tissue.
"Location" indicates the anatomic location of the TG tissue from which the T cell line was generated.
Data are the mean ± SD of two or three replicate experiments.
Percentages shown for the CD3+ CD4+ or CD3+ CD8+ subset, are corrected for mock control values.
NA, not available.

HSV-1 antigens. We use whole HSV-1 virus to document that TG-TCL (Table 1, FIGS. 2 and 3) and TCC recognize HSV-1. We selected the sequenced reference strain 17+ for whole virus and as the source of our ORFeome and random libraries. One caveat is divergence between HSV-1 strains (129). In general, amino acid (AA) variability is low between wild-type HSV-1 strains (~0.2-1% AA variation) (47, 130, 131).

Our main antigen format is a "virtual library" of every known HSV-1 ORF. HSV-1 has about 85 known ORFs (25). We obtained, as plasmids, 65 HSV-1 strain 17+ ORFs from Dr. Jurgen Haas (Munich, Germany). We PCR-cloned 18 of the 20 remaining ORFs (with high-fidelity DNA polymerase) from HSV-1 17+. Each was sequence-verified at both termini. We included all the more recently validated HSV-1 ORFs that are between or anti-sense to longer-recognized ORFs (25). Some long ORFs were cloned as ~500 amino acid segments overlapping by 20-30 amino acids. The only "missing" HSV-1 ORFs, ICP0 and ICP4, have been cloned in fragments and are being moved to our "destination" acceptor vector.

The entry vector we use allows rapid, no-PCR "flipping" of the "insert" into acceptor "destination" vectors (Gateway™). We built custom acceptor vector pDEST103. It expresses the HSV-1 ORF of interest "first" and then eGFP "in frame". To test pDEST103 in the T-cell context, we co-transfected Cos-7 cells with HLA B*0702 cDNA and pDEST103-UL49-HSV-2. At 48 hours, cloned, HLA B*0702-restricted, HSV-2 UL49 specific CD8 T-cells (20) were added. Supernatants (24 hours) tested by IFN-γ ELISA (20, 121) confirmed, strong, specific T-cell activation. We have "flipped" the entire HSV-1 proteome (sans ICP0 and ICP4) into pDEST103. UV microscopy of transfected Cos-7 shows green fluorescence for every ORF.

Discovery of HSV-1 T-cell antigens and epitopes recognized by human TG-infiltrating CD8 T-cells. We studied donor 14074 (HLA-A*0101, -B*0801) (Table 1, FIGS. 2&3). For synthetic APC, we co-transfected Cos-7 cells with HLA-A*0101 cDNA and the ORFeome set. Positive control APC was autologous LCL infected with HSV-1. Negative controls included uninfected autologous LCL. Responder bulk TG-infiltrating T-cells ($10^5$/well) were used to stress the system with polyclonal responders rather than a HSV-1-specific CD8 clone. At 24 hours of T-cell/APC contact, IFN-γ secretion was measured (20). We found reactivity with HSV-1 UL1 (glycoprotein L), UL53 (glycoprotein K), and UL48 (VP16). These are structural proteins with "early late" or "late" kinetics. They are not "immediate early" proteins that might be expected to be immunodominant in TG if CD8 T-cells specialized for detecting "early" reactivation.

Figure 4:
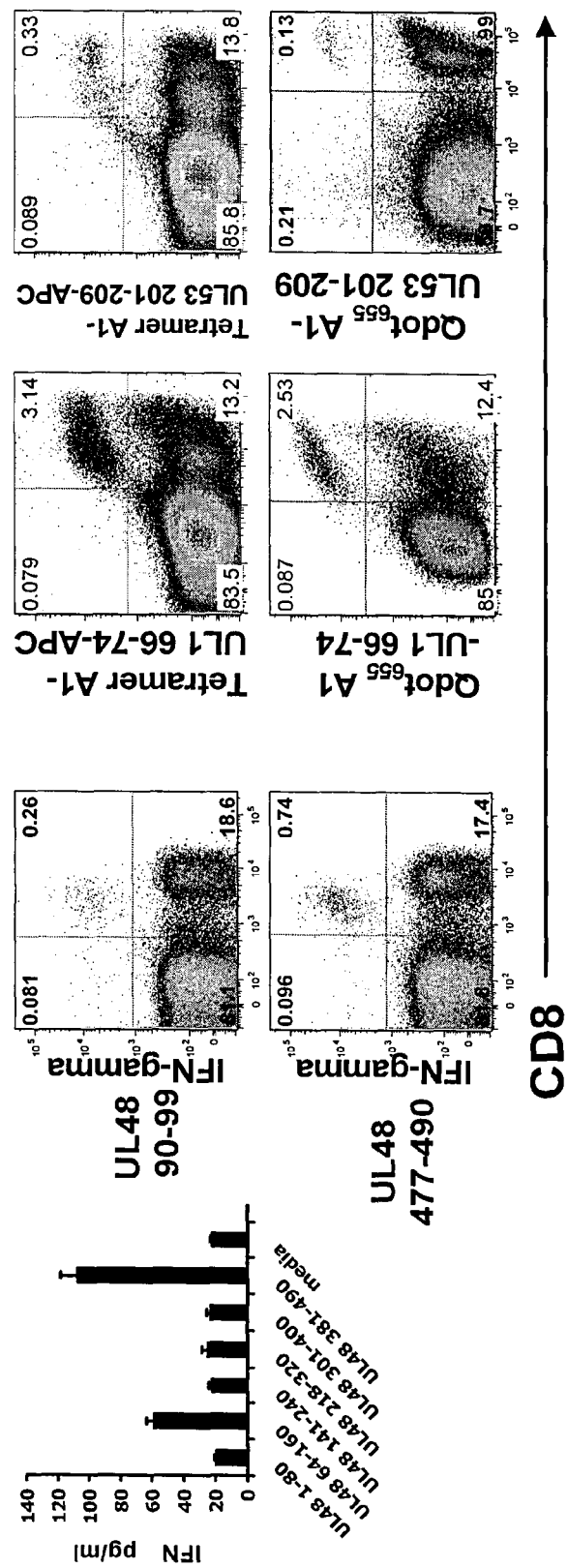
FIG. 4 shows that CD8 epitopes are recognized by HSV-1 specific T-cells in human TG. The bar graph at left shows IFN-γ secretion by TG24 bulk T cells to Cos-7 transfected with A*0101 and UL48 fragments (amino acids). The plots at left of center show IFN-γ responses to indicated UL48 peptides. The upper right panels show TG24 bulk T-cells stained with indicated UL1 and UL53 APC-labeled tetramers. The lower right panels show the same cells stained with Qdot$_{655}$ multimers made with the same HLA and peptides.

To validate that TG CD8 T-cells "see" these HSV-1 ORFs, peptides predicted (132) to bind HLA-A*0101 were synthesized, and then incubated (1 μM) with bulk TG T-cells, and LCL as APC (18). This strategy worked for UL1 and UL53. There was strong reactivity to UL1 AA 66-74 and UL53 AA 201-209 by IFN-γ ELISA. The EC50 concentrations were about 1 nanomolar. We did 6-hour IFN-γ ICC (114, 122) with autologous LCL and 1 μM peptide. Both peptides were reactive. Tetramers of HLA-A*0101 and peptide stained a discrete population of CD8 T-cells in the TG-TCL (FIG. 4).

For UL48, the initial peptides selected for possible HLA A*0101 binding were negative. Therefore, we cloned overlapping fragments in pDEST103, and tested them by HLA co-transfection. Two fragments were positive (FIG. 4, left). This allowed economical peptide synthesis of internal peptides. The first contains an epitope at AA 90-99, and the second at AA 477-490 (FIG. 4, center) in routine IFN-γ ICC. Negative control (DMSO) had <0.04% CD8 T-cells positive. These four HSV-1 epitopes are the first viral T-cell CD8 targets ever defined in human trigeminal ganglia.

We made HLA-A*0101-Qdot655 multimers of the novel UL1 and UL53 epitopes, and of a (−) control CMV peptide restricted by HLA A*0101. The advantages of the Qdots are discussed below. The UL1 and UL53 Qdots worked well (FIG. 4). The proportion of overall cells staining (+) was a little less for the Qdot655 multimers than for the tetramers (FIG. 4), but the Qdot stains used aged cultures. The CMV Qdot-multimer stain was negative. The Qdot655 multimers are for our first-line Aim 2 method.

We conclude that CD8 T-cells directed to diverse, structural, HSV-1 ORFs localize to HSV-1-infected human TG. It has been hypothesized that "immediate early" HSV proteins might best access HLA class I antigen presentation (97). We show that TG CD8 T-cells can react with "late" and structural proteins (20) (22, 109). These proteins must access HLA class I presentation pathways in ganglia. Neither arrays (112) nor northern blots (25), using "immediate early" conditions in vitro, or in human TG in vivo, have detected mRNA for these CD8 T-cell antigens. Local T-cells appear to be a sensitive, and perhaps temporally dispersed, probe.

REFERENCES CITED IN EXAMPLE 1
1. Verjans, G. M. et al. 2007. *Proc Natl Acad Sci USA* 104:3496-3501.
2. Knickelbein, J. E., et al. 2008. *Science* 322:268-271.
3. Koelle, D. M., and L. Corey. 2003. *Clin Microbiol Rev* 16:96-113.
4. Milligan, G. N., et al. 1998. *J. Immunol.* 160:6093-6100.
18. Koelle, D. M., et al. 2000. *J. Virol.* 74:10930-10938.
20. Koelle, D. M., et al. 2001. *J. Immunol.* 166:4049-4058.
22. Koelle, D. M., et al. 2003. *Proc Natl Acad Sci USA* 100:12899-12904.
25. Roizman, B., et al. 2007. In *Fields Virology*, Vol. 2nd. D. M. Knipe, Howley, P. M., ed. Lippincott, Williams, and Wilkins, Philadelphia, p. 2501-2602.
30. Verjans, G. M. et al. 1998. *J. Infect. Dis.* 177:484-488.
31. Verjans, G. M., et al. 1998. *J. Infect. Dis.* 178:27-34.
58. Cohrs, R. J., et al. 2000. *J Virol* 74:11464-11471.
97. Mikloska, Z., et al. 2000. *J. Immunol.* 164:5167-5176.
101. Gonzalez, J. C., et al. 2005. *J. Infect. Dis.* 191:243-254.
109. Hosken, N., et al. 2006. *J. Virol.* 80:5509-5515.
110. Tigges, M. A., et al. 1992. *J. Virol.* 66:1622-1634.
112. Stingley, S. W., et al. 2000. *J Virol* 74:9916-9927.
114. Jing, L., et al. 2005. *J Immunol* 175:7550-7559.
115. Jing, L., et al. 2007. *J Immunol* 178:6374-6386.
119. Kawakami, A., et al. 1994. *J Immunol* 152:4937-4945.
120. van Dongen, J. J., et al. 2003. *Leukemia* 17:2257-2317.
121. Koelle, D. M. 2003. *Methods* 29:213-226.
122. Jing, L., et al. 2008. *J Virol.*
123. Jing, L., et al. 2007. *J. Immunol. Submitted.*
124. Munks, M. W., et al. 2006. *J Immunol* 176:3760-3766.
125. Tscharke, D. C., et al. 2006. *J Virol* 80:6318-6323.
126. Munks, M. W., et al. 2007. *J Immunol* 178:7235-7241.
127. Tigges, M. A., et al. 1996. *J. Immunol.* 156:3901-3910.
128. Yasukawa, M., and Y. Kobayashi. 1985. *J. Gen. Virol.* 66:2225-2229.
129. McGeoch, D. J., et al. 1988. *J. Gen. Virol.* 69:1531-1574.
132. Sette, A., et al. 2005. *Immunity* 22:155-161.

Example 2

HSV-1 T-Cell Antigens and Epitopes Recognized by CD4 T-Cells of TG

Further studies have identified two regions in the HSV-1 UL48 protein that are recognized by CD4 T-cells in the human trigeminal ganglia. The large fragments of amino acids 141-240 and amino acids 218-320 were reactive in the CD4 cell tests. To follow up, we showed that amino acids 187-199 (VRQLHRQAHMRGR; SEQ ID NO: 10) and the overlapping region amino acids 191-203 (HRQAHMRGRDRDL; SEQ ID NO: 11) were both reactive. It is likely that there is a small region of the UL48 protein that is contained in the overlap region that is the minimum reactive region, e.g. at or near amino acids 191-199. We also showed that amino acids 215-227 (YYRETARLARVLF; SEQ ID NO: 12) and the overlapping amino acids 219-230(TARLARVLFLHL; SEQ ID NO: 13) were reactive with CD4 T cells. Again, it is likely that there is a minimal reactive region in the overlap of these two, e.g. at or near amino acids 219-227.

Example 3

HSV-1 T-Cell Antigens and Epitopes Relevant to a Significant Population

The regions of HSV-1 UL1, UL48, and UL53 that stimulate CD8 T-cells were found in a subject who has the A*0101 variant of the human gene HLA-A. From 10% to 20% of many ethnic and national populations have the HLA type A*0101. The precise genetic variant possessed by different persons controls which portions of which viral proteins their T-cells can recognize. However, it is not always true that regions of viruses are recognized by all persons who have the correct HLA genetic variant. Antigenic regions that are recognized by most or all persons with the relevant HLA genetic variant are more likely to be of interest for use in a vaccine. To test this, we studied 3 random healthy persons who have HSV-1 infection and HLA A*0101. For each person, all three of the peptides UL1 66-74, UL53 201-209, and UL48 90-99 were strongly recognized by 3 out of 3 people. This supports their utility in vaccines.

Example 4

UL1 and UL53 Epitopes are Type Common to HSV-1 and HSV-2

Figure 5A:
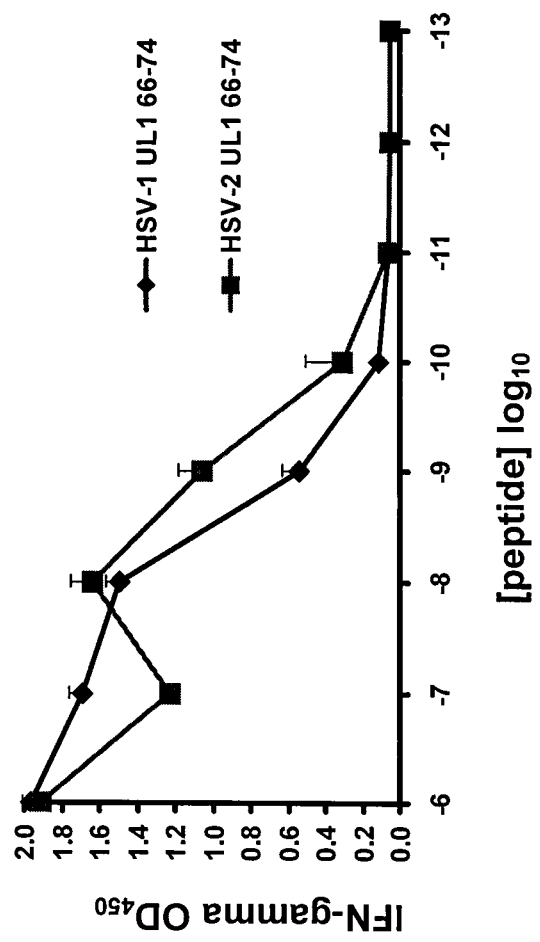
FIGS. 5A-5B are graphs showing results of a 24-hour IFN-γ release assay with LCL used at APC. The diamond symbols represent results obtained using the HSV-1 peptide sequence for UL1 (FIG. 5A) or UL53 (FIG. 5B); while the square symbols represent results obtained with the corresponding HSV-2 peptide.
Figure 5B:
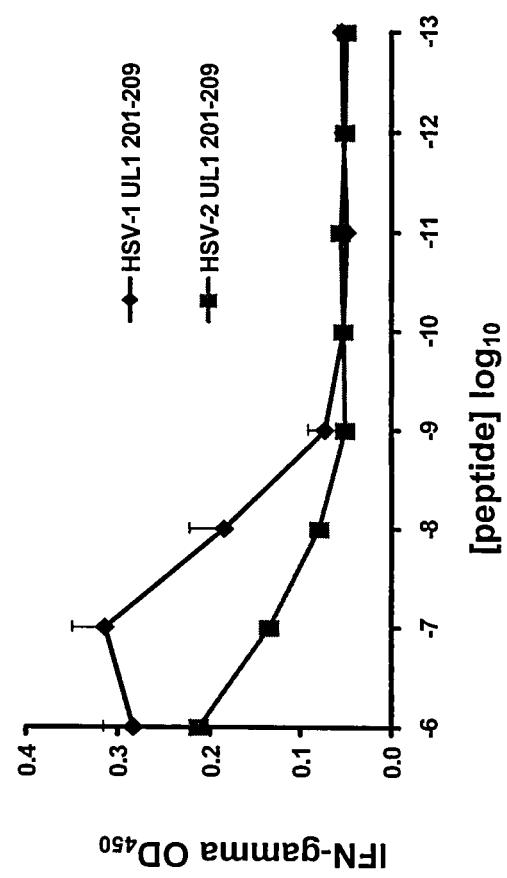

A 24-hour IFN-γ release assay with LCL used at APC was performed with the UL1 and UL53 epitopes. The results show that the HSV UL1 and UL53 epitopes identified herein have an $EC_{50}$ of $10^{-8}$ to $10^{-9}$ molar. In addition, comparison of the HSV-1 UL1 peptide at amino acids 66-74, LIDGIFLRY (SEQ ID NO: 6) with the corresponding HSV-2 UL1 peptide at amino acids 66-74, RIDGIFLRY (SEQ ID NO: 8), showed that HSV-1 UL1 specific T cells recognize peptides with similar but not identical sequences from HSV-2 (FIG. 5A). Likewise, comparison of the HSV-1 UL53 peptide at amino acids 201-209, ETDPVTFLY (SEQ ID NO: 7) with the corresponding HSV-2 UL53 peptide at amino acids 201-209, EADPVTFLY (SEQ ID NO: 9), showed that HSV-1 UL53 specific T cells also recognize peptides with similar but not identical sequences from HSV-2 (FIG. 5B).

Example 5

Identification of Minimal Fully Active Epitope within UL48 477-490

Further studies have tested fragments within amino acids 477-490 of UL48/VP16 to identify the minimal epitope. The 11mer peptide 479-489, and the 10mer peptide 479-488 were fully biologically active. The 9mer peptide 480-488 was also active, but less active than the 479-488 peptide. Therefore the minimal fully active peptide is the 10mer 479-488.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A pharmaceutical composition comprising an isolated HSV-1 polypeptide, wherein the HSV-1 polypeptide comprises an immunogenic portion of VP16, and a pharmaceutically acceptable carrier, wherein the polypeptide consists of amino acids: 64-160, 90-99, 141-240, 187-199, 191-203, 215-227, 218-320, 219-230, 381-490, 479-489, 479-488, 480-488 or 477-490 of VP16 (SEQ ID NO: 1) and up to 50 amino acids of adjacent sequence of the original protein of SEQ ID NO: 1; optionally fused to a heterologous polypeptide, wherein the heterologous polypeptide is selected from glycoprotein L (SEQ ID NO: 2), glycoprotein K (SEQ ID NO: 3), or a fragment or combination thereof.

2. The pharmaceutical composition of claim 1, wherein the polypeptide is a fusion protein comprising the isolated HSV polypeptide fused to glycoprotein L (SEQ ID NO: 2) or glycoprotein K (SEQ ID NO: 3).

3. The pharmaceutical composition of claim 2, wherein the fusion protein is soluble.

4. The pharmaceutical composition of claim 1, further comprising an adjuvant.

5. A HSV polypeptide produced by culturing a host cell transformed with a vector comprising a polynucleotide encoding an immunogenic portion of a VP16 polypeptide, wherein the polypeptide consists of amino acids 64-160, 90-99, 141-240, 187-199, 191-203, 215-227, 218-320, 219-230, 381-490, 479-489, 479-488, 480-488 or 477-490 of VP16 and up to 50 amino acids of adjacent sequence of the original protein of SEQ ID NO: 1, and recovering the polypeptide so produced.

6. A method of enhancing proliferation of HSV-specific T cells comprising contacting the HSV-specific T cells with an isolated polypeptide that comprises an immunogenic portion of VP16, wherein the polypeptide consists of amino acids 64-160, 90-99, 141-240, 187-199, 191-203, 215-227, 218-320, 219-230, 381-490, 479-489, 479-488, 480-488 or 477-490 of VP16 and up to 50 amino acids of adjacent sequence of the original protein of SEQ ID NO: 1.

7. A method of inducing an immune response to an HSV infection in a subject comprising administering the composition of claim 1 to the subject.

8. A method of treating a HSV infection in a subject comprising administering the composition of claim 1 to the subject.

9. The pharmaceutical composition of claim 1, wherein the polypeptide is a fusion protein comprising glycoprotein L (SEQ ID NO: 2), glycoprotein K (SEQ ID NO: 3), or a fragment or combination thereof.

10. The pharmaceutical composition of claim 9, wherein the fragment comprises amino acids 66-74 of glycoprotein L (ETDPVTFLY; SEQ ID NO: 6 or EADPVTFLY; SEQ ID NO: 8), or amino acids 201-209 of glycoprotein K (LIDGIFLRY; SEQ ID NO: 7 or RIDGIFLRY; SEQ ID NO: 9).

11. The pharmaceutical composition of claim 1, wherein the HSV-1polypeptide consists of amino acids 90-99 or 479-488 of VP16 and up to 50 amino acids of adjacent sequence of the original protein of SEQ ID NO: 1.

12. The method of claim 7, wherein the immune response comprises killing a HSV infected cell.

13. The method of claim 7, wherein the immune response comprises inhibiting HSV replication.

14. The method of claim 7, wherein the immune response comprises enhancing secretion of antiviral or immunomodulatory lymphokines.

15. The method of claim 7, wherein the immune response comprises enhancing production of HSV-specific antibody.

16. The method of claim 7, wherein the immune response comprises enhancing proliferation of HSV-specific T cells.

* * * * *

UNITED STATES PATENT AND TRADEMARK OFFICE
Certificate

Patent No. 8,460,674 B2            Patented: June 11, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David M. Koelle, Seattle, WA (US); and George M. G. M. Verjans, Doetinchem (NL).

Signed and Sealed this Twenty-fifth Day of November 2014.

ZACHARIAH LUCAS
*Supervisory Patent Examiner*
Art Unit 1648
Technology Center 1600